US009554790B2

(12) United States Patent
Bailey et al.

(10) Patent No.: US 9,554,790 B2
(45) Date of Patent: Jan. 31, 2017

(54) ROBOTIC ENDOSCOPIC RETRACTOR FOR USE IN MINIMALLY INVASIVE SURGERY

(71) Applicant: INTUITIVE SURGICAL OPERATIONS, INC., Sunnyvale, CA (US)

(72) Inventors: David W. Bailey, Redwood City, CA (US); Michael H. Ikeda, Saratoga, CA (US); Margaret M. Nixon, Santa Clara, CA (US); Hubert Stein, San Francisco, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 15/072,080

(22) Filed: Mar. 16, 2016

(65) Prior Publication Data

US 2016/0270773 A1   Sep. 22, 2016

Related U.S. Application Data

(63) Continuation of application No. 14/079,403, filed on Nov. 13, 2013, now Pat. No. 9,314,153, which is a continuation of application No. 11/479,614, filed on Jun. 30, 2006, now Pat. No. 8,597,182.

(60) Provisional application No. 60/795,804, filed on Apr. 28, 2006.

(51) Int. Cl.
| | |
|---|---|
| *A61B 1/32* | (2006.01) |
| *A61B 17/02* | (2006.01) |
| *A61B 1/00* | (2006.01) |
| *A61B 1/313* | (2006.01) |

(52) U.S. Cl.
CPC ....... *A61B 17/0218* (2013.01); *A61B 1/00087* (2013.01); *A61B 1/313* (2013.01); *A61B 1/32* (2013.01); *A61B 34/30* (2016.02); *A61B 34/37* (2016.02); *A61B 34/70* (2016.02); *A61B 34/71* (2016.02); *A61B 2017/0225* (2013.01); *A61B 2017/0237* (2013.01); *A61B 2034/305* (2016.02)

(58) Field of Classification Search
CPC combination set(s) only.
See application file for complete search history.

(56) References Cited

U.S. PATENT DOCUMENTS

| | | | |
|---|---|---|---|
| 3,667,474 A | 6/1972 | Lapkin et al. | |
| 5,353,784 A * | 10/1994 | Nady-Mohamed | A61B 17/0218 600/205 |
| 5,993,385 A | 11/1999 | Johnston et al. | |
| 6,206,903 B1 | 3/2001 | Ramans | |
| 6,564,805 B2 | 5/2003 | Garrison et al. | |
| 6,673,041 B1 | 1/2004 | Macoviak | |
| 6,676,684 B1 | 1/2004 | Morley et al. | |
| 6,764,445 B2 | 7/2004 | Ramans et al. | |

(Continued)

OTHER PUBLICATIONS

Intuitive Surgical, Solutions for Minimally Invasive Cardiothoracic Surgery, da Vinci Mitral Valve Repair, 6 pages.

(Continued)

*Primary Examiner* — Sameh Boles

(57) ABSTRACT

Minimally invasive surgical retractors and methods of using the retractors are provided. This retractor may be introduced through a sealed port, controlled by a robotic system, have full articulation, and need not require assembly within the patient's body. As a result, fully endoscopic mitral valve surgery may be performed.

9 Claims, 22 Drawing Sheets

(56) References Cited

U.S. PATENT DOCUMENTS

| | | |
|---|---|---|
| 6,899,704 B2 | 5/2005 | Sterman et al. |
| 6,902,560 B1 | 6/2005 | Morley et al. |
| 8,597,182 B2 | 12/2013 | Stein et al. |
| 2004/0082837 A1 | 4/2004 | Willis |
| 2005/0119530 A1 | 6/2005 | Douglas et al. |
| 2014/0073856 A1 | 3/2014 | Stein et al. |

OTHER PUBLICATIONS

Mehmanesh, Hormoz et al., "Totally endoscopic mitral valve repair," The Journal of Thoracic and Cardiovascular Surgery, Jan. 2002, pp. 96-97, vol. 123, No. 1.

Navia, Jose Luis, "Minimally Invasive Mitral Valve Surgery," The Department of Thoracic and Cardiovascular Surgery, The Cleveland Clinic Foundation, 10 pages.

Vertut, Jean and Phillipe Coiffet, Robot Technology; Teleoperation and Robotics Evolution and Development, English translation, Prentice-Hall, Inc., Inglewood Cliffs, NJ, USA 1986, vol. 3A, 332 pages.

* cited by examiner

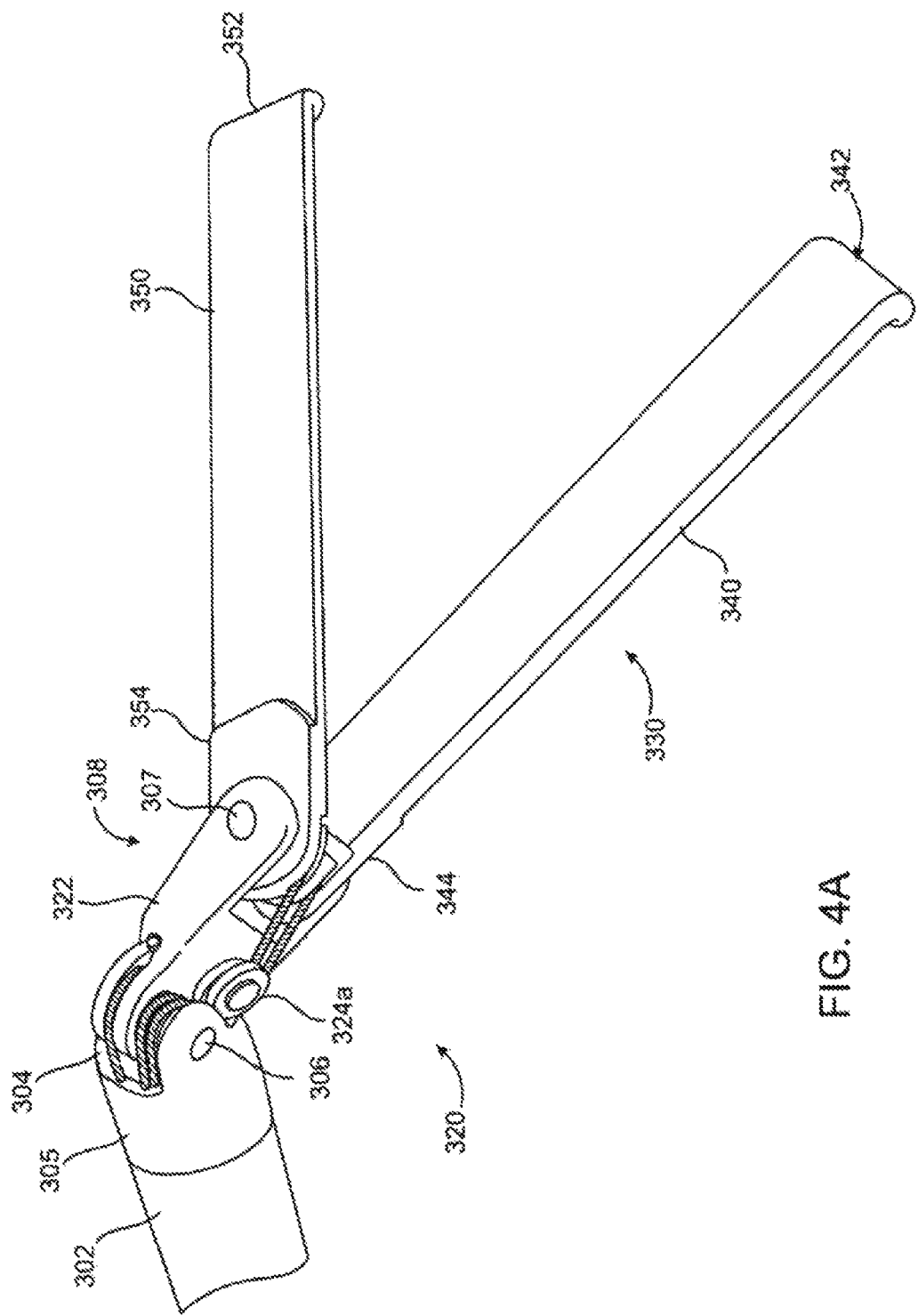

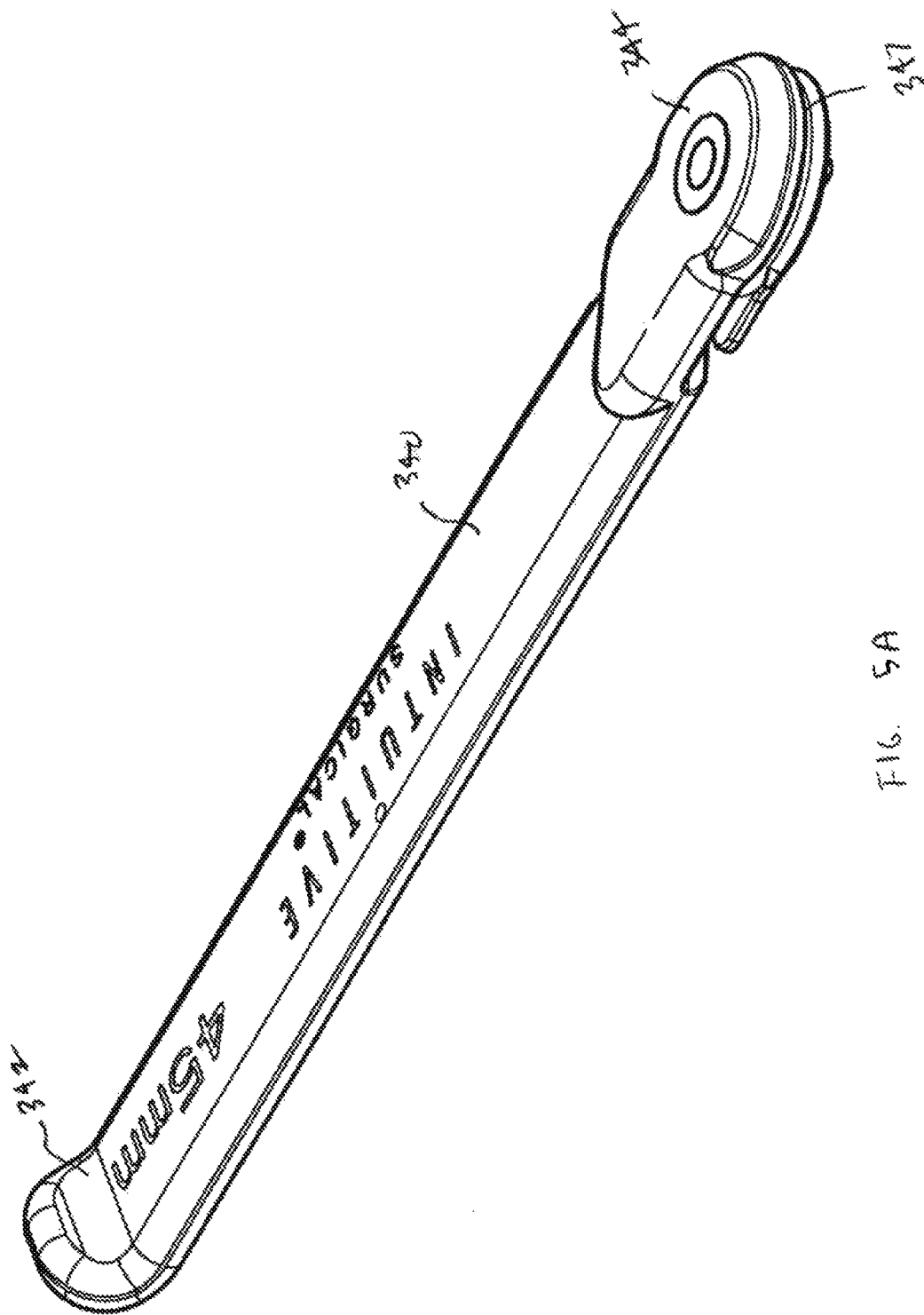

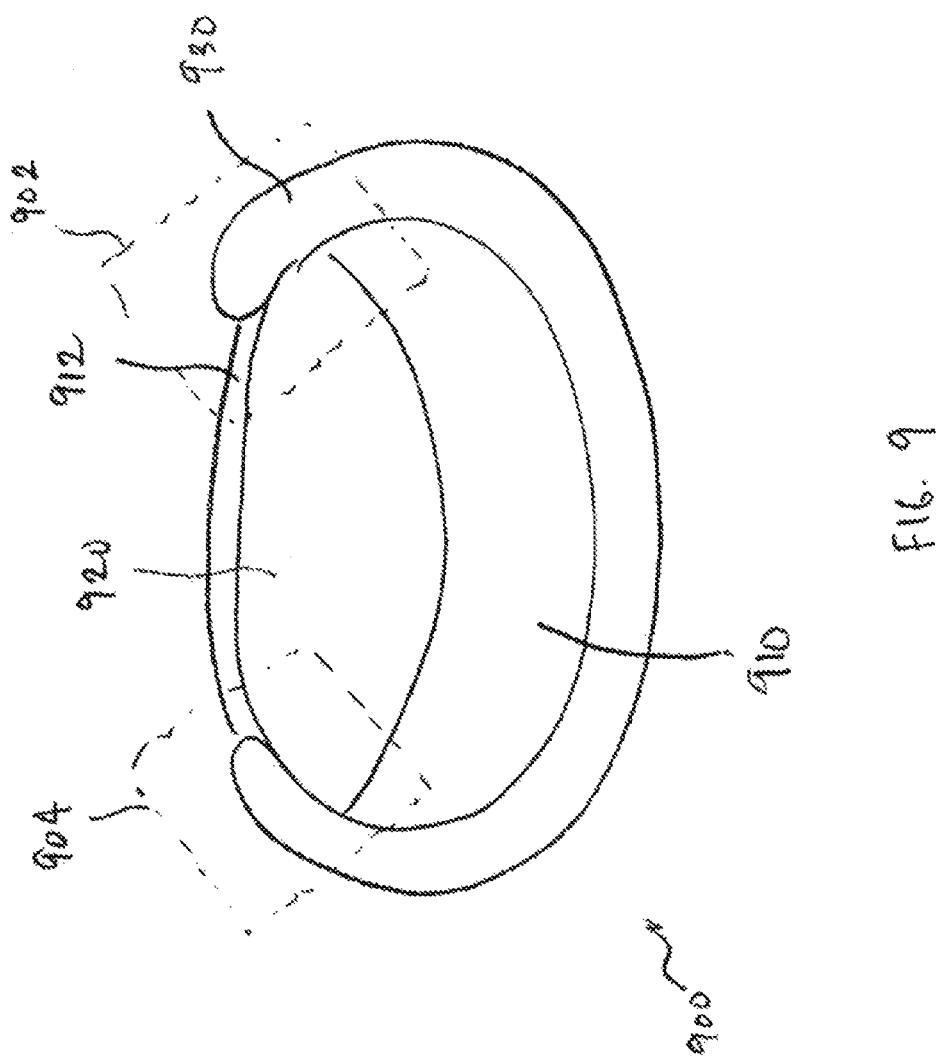

ROBOTIC ENDOSCOPIC RETRACTOR FOR USE IN MINIMALLY INVASIVE SURGERY

CROSS-REFERENCE TO RELATED APPLICATIONS

This application is a continuation of U.S. patent application Ser. No. 14/079,403, filed Nov. 13, 2013 which claims the benefit of the priority from U.S. Non-Provisional patent application Ser. No. 11/479,614, filed on Jun. 30, 2006, entitled "ROBOTIC ENDOSCOPIC RETRACTOR FOR USE IN MINIMALLY INVASIVE SURGERY," and U.S. Provisional patent application Ser. No. 60/795,804, filed on Apr. 28, 2006, entitled "ROBOTIC ENDOSCOPIC RETRACTOR FOR USE IN MINIMALLY INVASIVE SURGERY," the disclosures of which are incorporated herein in their entirety.

BACKGROUND

Mitral valve surgery has traditionally been performed through the median sternotomy in which the left atrium of the heart is opened and exposed to allow reconstruction of the mitral valve. More recently, minimally invasive techniques have been used for mitral valve surgery. Minimally invasive techniques are aimed at reducing the amount of extraneous tissue that is damaged during diagnostic or surgical procedures, thereby reducing patient recovery time, discomfort, and deleterious side effects.

One minimally invasive mitral valve repair technique is illustrated in FIG. 1. After opening of the atrium, an atrial retractor 100 is used to expose and stabilize the septum to create space for movement of laparoscopic instruments. The atrial retractor 100 includes a retractor blade 102 and a retractor rod 104. The retractor blade is available in different sizes. Typically, blades which are 50 mm long and 25 to 35 mm wide are used. The retractor blade 102 is inserted through a lateral thoracotomy of sufficient size to allow the blade 102 to pass through (e.g., approximately a 3.5 to 5 cm incision). The retractor rod 104 is inserted into the thorax through an incision 108 in the second or third intercostal space just 2 to 3 cm laterally to the sternum in the right chest. The retractor blade 102 is then attached to the retractor rod 104, typically using a screw mechanism.

The atrial retractor is positioned in the right atrium so as to retract the atrial wall to provide satisfactory exposure of the mitral valve annulus and subvalvular structure. The retractor rod 104 is secured in place using a stable structure, such as a holding arm, the operating table, or the patient's chest.

One disadvantage of transthoracic mechanical retractors, such as the atrial retractor 100, is that a thoracotomy is still required in order to introduce the atrial retractor, thereby preventing a fully endoscopic approach to mitral valve repair. In addition, during a robotic assisted mitral valve operation with the da Vinci Surgical System by Intuitive Surgical, Inc. of Sunnyvale, Calif., the insertion of the retractor blade 102, the attaching of the blade 102 and rod 104, and locking and securing of the rod 104 to the holding arm are typically performed while the robotic arm cart is docked to the patient, thereby constraining the workspace for the patient side surgeon. The size of the blade 102 that can be utilized is also limited by space limitations of the thoracotomy and within the patient's body.

Furthermore, the assembly of the retractor 100 is cumbersome and counter-intuitive. The patient side surgeon typically aligns the retractor blade 102 and the rod 104 laparoscopically. If the surgeon is not laparoscopically trained, the assembly time and time to mitral valve exposure can be long and frustrating.

The quality of the mitral valve exposure may vary dramatically from patient to patient, depending on where the retractor rod 104 enters the thoracic cavity. The incision serves as a fixed pivot point for the rigid retractor rod 104, thereby limiting the adjustment of positioning of the retractor blade 102.

In some cases, the retractor rod 104 may collide with the robotic camera arm, thereby decreasing the mitral valve exposure and obstructing the surgeon's view. Moreover, once the retractor 100 is positioned, repositioning later in the procedure may be difficult or impossible. When reposition is possible, the patient side assistant will typically have to perform multiple maneuvers to unlock and readjust the atrial retractor 100, which can be time consuming and cumbersome.

Finally, these retractors may introduce air into the aortic root due to distortion of the aortic valve.

Accordingly, there is a need for an improved retractor which may be used for minimally invasive heart valve repair and other surgical procedures.

SUMMARY

A minimally invasive surgical retractor is provided. This retractor may be introduced through a sealed port, controlled by a robotic system, have full articulation, and need not require assembly within the patient's body. As a result, fully endoscopic mitral valve surgery may be performed.

In accordance with embodiments of the present invention, a minimally invasive surgical instrument is provided, including: an elongate shaft; and a retractor assembly coupled to a distal end of the elongate shaft, the retractor assembly comprising a pair of blades, each blade having a mounting end coupled to a pivot point and an opposing free end, wherein said pair of blades are substantially overlapped when in a closed position and having the opposing free ends angularly displaced from each other when in an open position.

In accordance with embodiments of the present invention, a method of performing minimally invasive endoscopic surgery in a body cavity of a patient is provided, the method comprising: introducing an elongate shaft into the cavity, the elongate shaft having a proximal end, a shaft coupled to the proximal end, a wrist assembly coupled to the shaft, and a retractor assembly coupled to the wrist assembly, said retractor assembly comprising a pair of blades, each blade having a mounting end coupled to the wrist assembly and an opposing free end; deploying the retractor assembly inside the cavity by angularly displacing the free ends of the pair of blades; and retracting tissue using the retractor assembly.

Other features and aspects of the invention will become apparent from the following detailed description, taken in conjunction with the accompanying drawings which illustrate, by way of example, the features in accordance with embodiments of the invention. The summary is not intended to limit the scope of the invention, which is defined solely by the claims attached hereto.

DESCRIPTION OF THE DRAWINGS

FIGS. 4A-4C are an enlarged perspective views of the working end of the surgical instrument, including a wrist assembly and retractor assembly.

FIGS. 5A and 5B are front and rear perspective views of an inner blade of the retractor assembly.

FIG. 9 is a simplified view of a mitral valve with an annuloplasty ring attached thereto.

DETAILED DESCRIPTION

Figure 1:
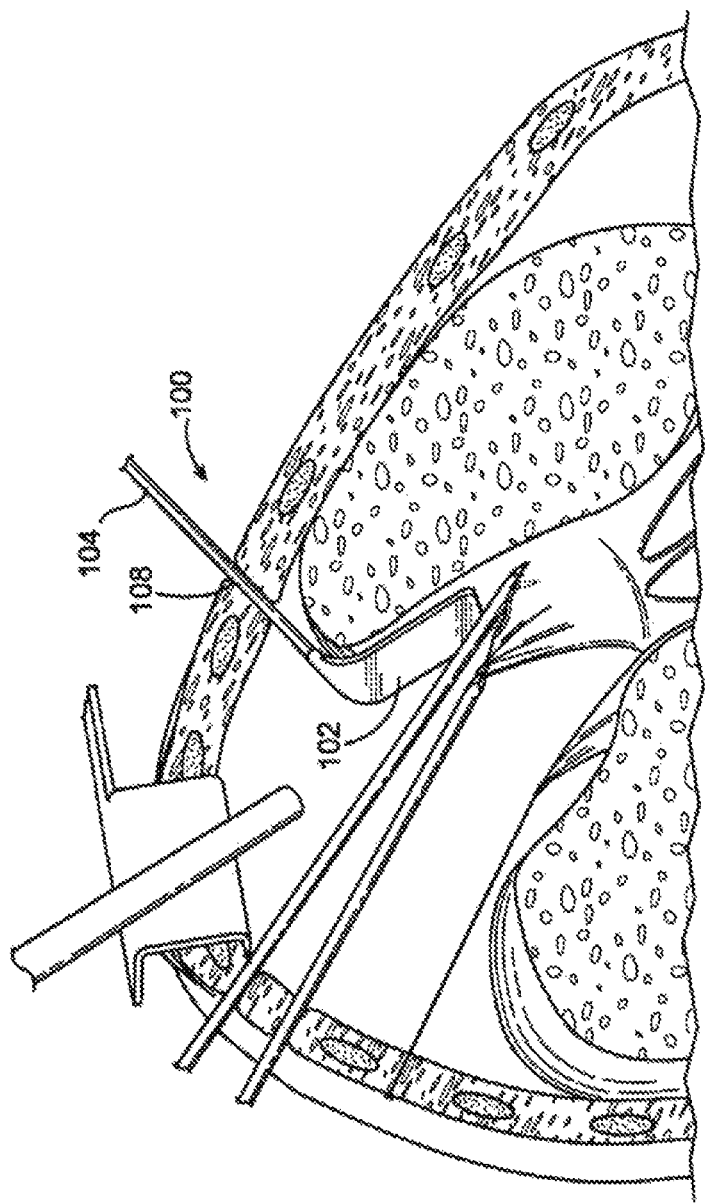
FIG. 1 illustrates a mitral valve repair procedure utilizing a conventional atrial retractor.

In the following description, reference is made to the accompanying drawings which illustrate several embodiments of the present invention. It is understood that other embodiments may be utilized and mechanical, compositional, structural, electrical, and operational changes may be made without departing from the spirit and scope of the present disclosure. The following detailed description is not to be taken in a limiting sense, and the scope of the embodiments of the present invention is defined only by the claims of the issued patent.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Robotic surgery systems, devices, and methods are described. Robotic surgery will generally involve the use of multiple robotic arms. One or more of the robotic arms will often support a surgical tool which may be articulated (such as jaws, scissors, graspers, needle holders, microdissectors, staple appliers, tackers, suction/irrigation tools, clip appliers, or the like) or non-articulated (such as cutting blades, cautery probes, irrigators, catheters, suction orifices, or the like). One or more of the robotic arms will often be used to support one or more surgical image capture devices such as an endoscope (which may be any of the variety of structures such as a laparoscope, an arthroscope, a hysteroscope, or the like), or optionally, some other imaging modality (such as ultrasound, fluoroscopy, magnetic resonance imaging, or the like). Typically, the robotic arms will support at least two surgical tools corresponding to the two hands of a surgeon and one optical image capture device. A fourth robotic arm may be provided to support a positionable retractor assembly, as will be described in greater detail below.

Positionable retractor instruments may be utilized in a variety of surgical procedures. The most immediate applications will be to improve existing minimally invasive surgical procedures, such as mitral and aortic valve repair and/or replacement. Additionally, it is anticipated that these surgical systems will find uses in entirely new surgeries that would be difficult and/or impossible to perform using traditionally open or known minimally invasive techniques. Additional potential applications include vascular surgery (such as for the repair of thoracic and abdominal aneurysms), general and digestive surgeries (such as cholecystectomy, inguinal hernia repair, colon resection, and the like), gynecology (for fertility procedures, hysterectomies, and the like), and a wide variety of alternative procedures.

Figure 2:
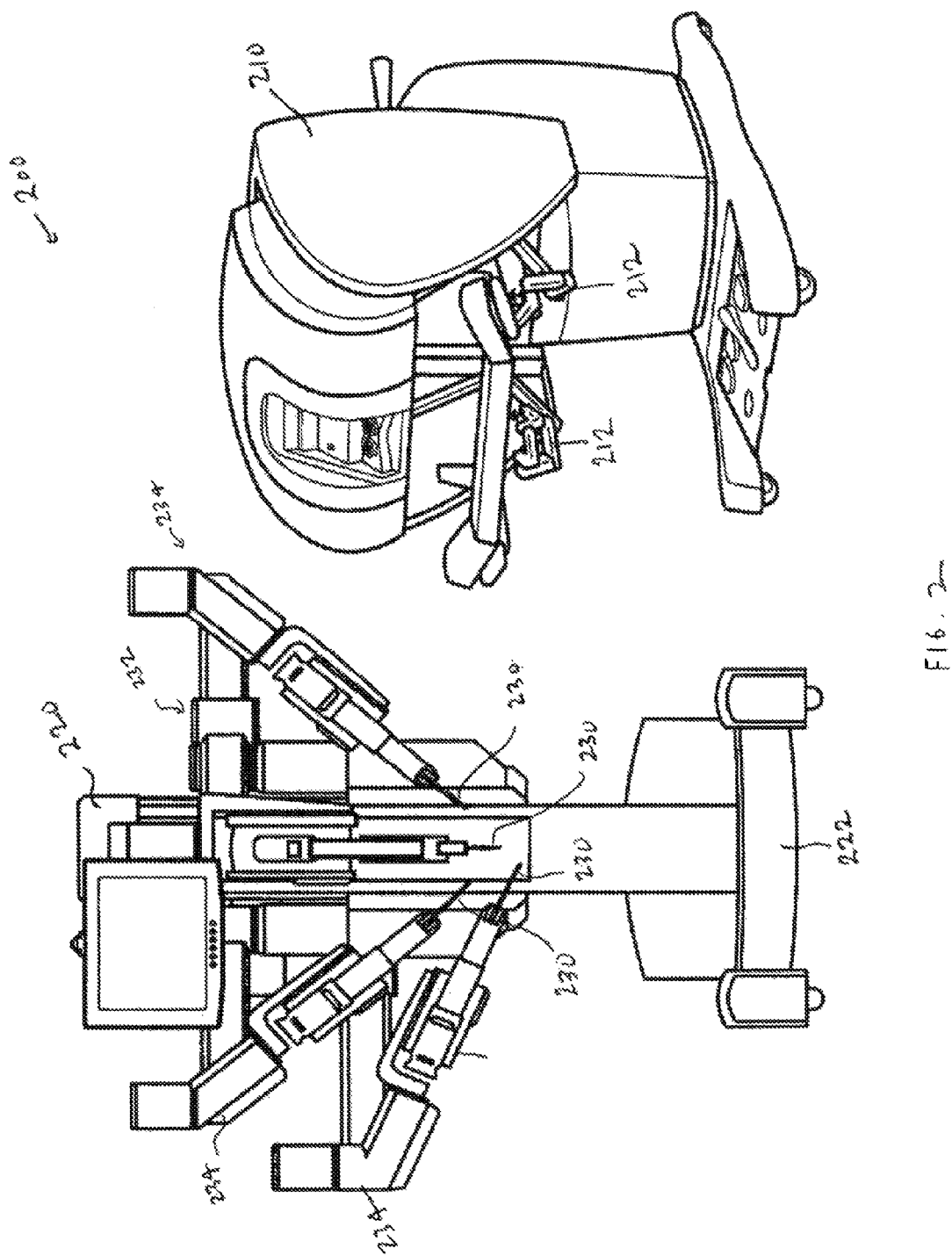
FIG. 2 shows a robotic surgical system including a master control station and a robotic arm cart.

FIG. 2 shows a robotic surgical system 200 including a master control station 210 coupled to a robotic arm cart 220. The master control station 210 generally includes master controllers 212 which are grasped by the surgeon and manipulated in space while the surgeon views the procedure views a stereo display. The master controllers 212 are manual input devices which may move with six degrees of freedom, and which often further have an actuatable handle for actuating instruments (for example, for closing grasping saws, applying an electrical potential to an electrode, or the like). The master control station 210 may also include a processor.

The robotic arm cart 220 is positioned adjacent to the patient's body and moves instruments having shafts. The shafts extend into an internal surgical site within the patient body via openings in the body. One or more assistants may be present during surgery to assist the surgeon, particularly during removal and replacement of instruments. Robotic surgery systems and methods are further described in U.S. Pat. No. 5,797,900, filed on May 16, 1997, issued on Aug. 25, 1998, U.S. Pat. No. 6,132,368, filed on Nov. 21, 1997, issued on Oct. 17, 2000, U.S. Pat. No. 6,331,181, filed on Oct. 15, 1999, issued on Dec. 18, 2001, U.S. Pat. No. 6,441,577, filed on Apr. 3, 2001, issued on Aug. 27, 2002, U.S. Pat. No. 6,902,560, filed on Jan. 6, 2004, issued on Jun. 7, 2005, U.S. Pat. No. 6,936,042, filed on Apr. 16, 2002, issued on Aug. 30, 2005, and U.S. Pat. No. 6,994,703, filed on Dec. 4, 2002, issued on Feb. 7, 2006, the full disclosures of which are incorporated herein by reference. A suitable robotic surgical system currently in use is the da Vinci S Surgical System by Intuitive Surgical, Inc.

The robotic arm cart 220 includes a base 222 from which four surgical instruments 230 are supported. More specifically, the surgical instruments 230 are each supported by a series of manually articulatable linkages, generally referred to as set-up joints 232, and a robotic manipulator 234. The robotic manipulators 234 enable the instrument 230 to be rotated around a point in space, as more fully described in issued U.S. Pat. Nos. 6,331,181, and 5,817,084, the full disclosures of which are incorporated herein by reference. The robotic manipulators 234 pivot the instrument 230 about a pitch axis, a yaw axis, and an insertion axis (which is aligned along a shaft of the instrument 230). The instrument 230 has still further driven degrees of freedom as supported by the manipulator 234, including sliding motion of the instrument 230 along the insertion axis.

The robotic manipulators 234 are driven by a series of motors. These motors actively move the robotic manipulators 234 in response to commands from a processor. The motors are further coupled to the instrument 230 so as to rotate the instrument 230 about the insertion axis, and often to articulate a wrist at the distal end of the instrument about at least one, and often two, degrees of freedom. Additionally, the motors can be used to actuate an articulatable end effector of the instrument for grasping tissues in the jaws of a forceps or the like. The motors may be coupled to at least some of the joints of instrument 230 using cables, as more fully described in U.S. Pat. Nos. 6,331,181, and 5,792,135, the full disclosures of which are also incorporated herein by reference. As described in those references, the manipulators 234 will often include flexible members for transferring motion from the drive components to the surgical instrument. For endoscopic procedures, the manipulators 234 may include a cannula, which supports the instrument 230, allowing the instrument 230 to rotate and move axially through the central bore of the cannula.

Figure 3:
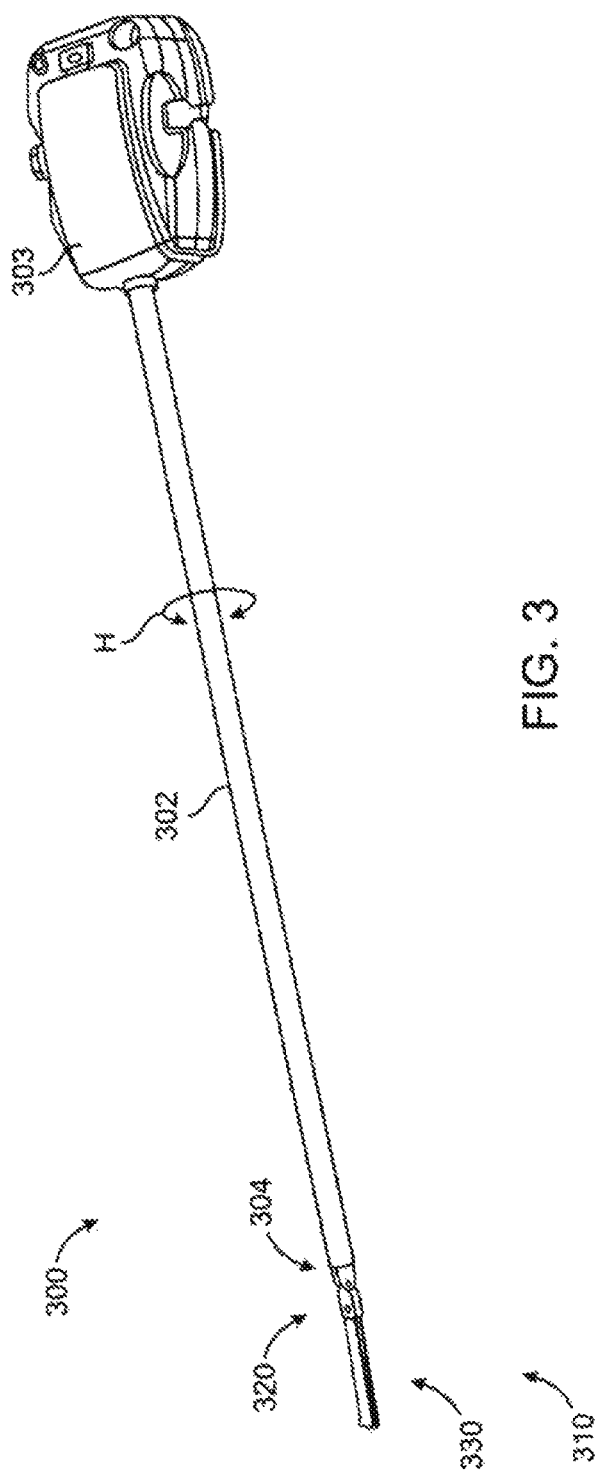
FIG. 3 illustrates a surgical instrument, in accordance with embodiments of the present invention.

FIG. 3 illustrates a surgical instrument 300, including a shaft portion 302, a control housing 303 provided at a proximal end of the shaft portion 302, and a working end 310 at a distal end of the shaft portion 302. The working end 310 comprises a wrist assembly 320 coupled to a proximal clevis assembly 304 provided at a distal end of the shaft portion 302, and a retractor assembly 330 coupled to the wrist mechanism 320. When the surgical instrument 300 is coupled or mounted onto the robotic manipulator 234, the shaft portion 302 extends along the instrument axis. A similar robotic manipulator and surgical instrument is described in U.S. Pat. No. 6,902,560, the disclosure of which is incorporated by reference herein in its entirety.

Figure 4B:
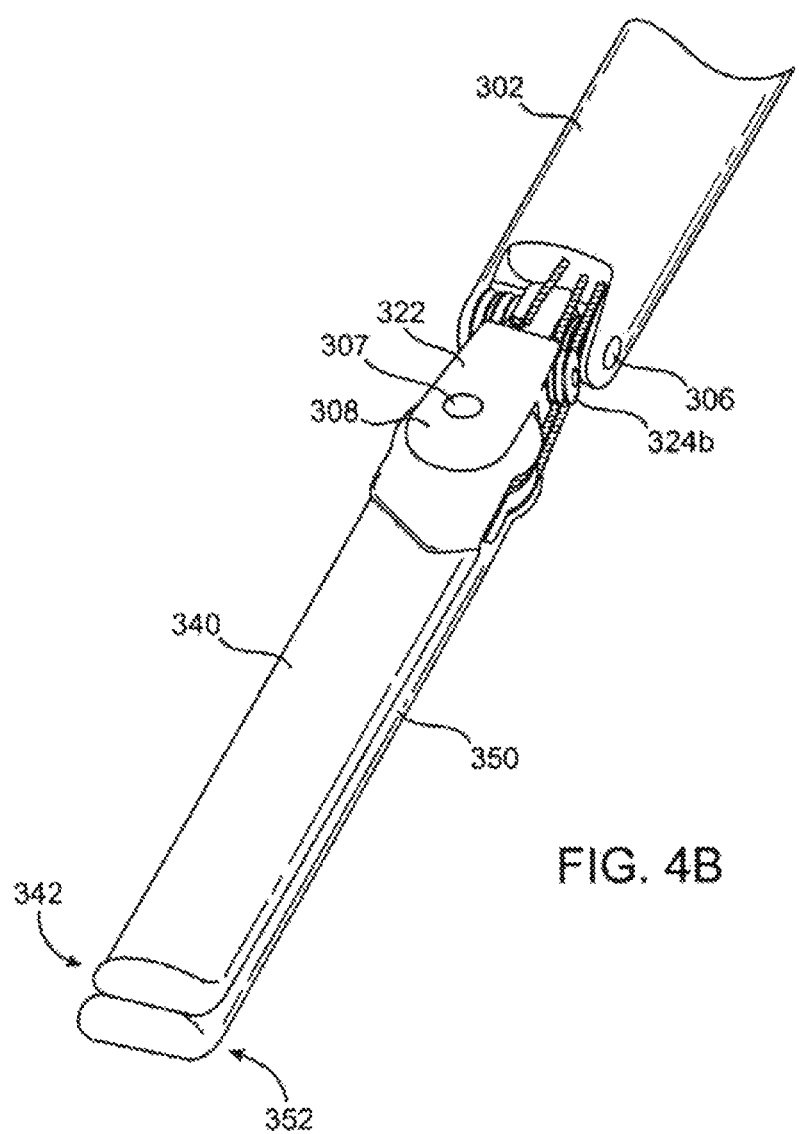
Figure 4C:
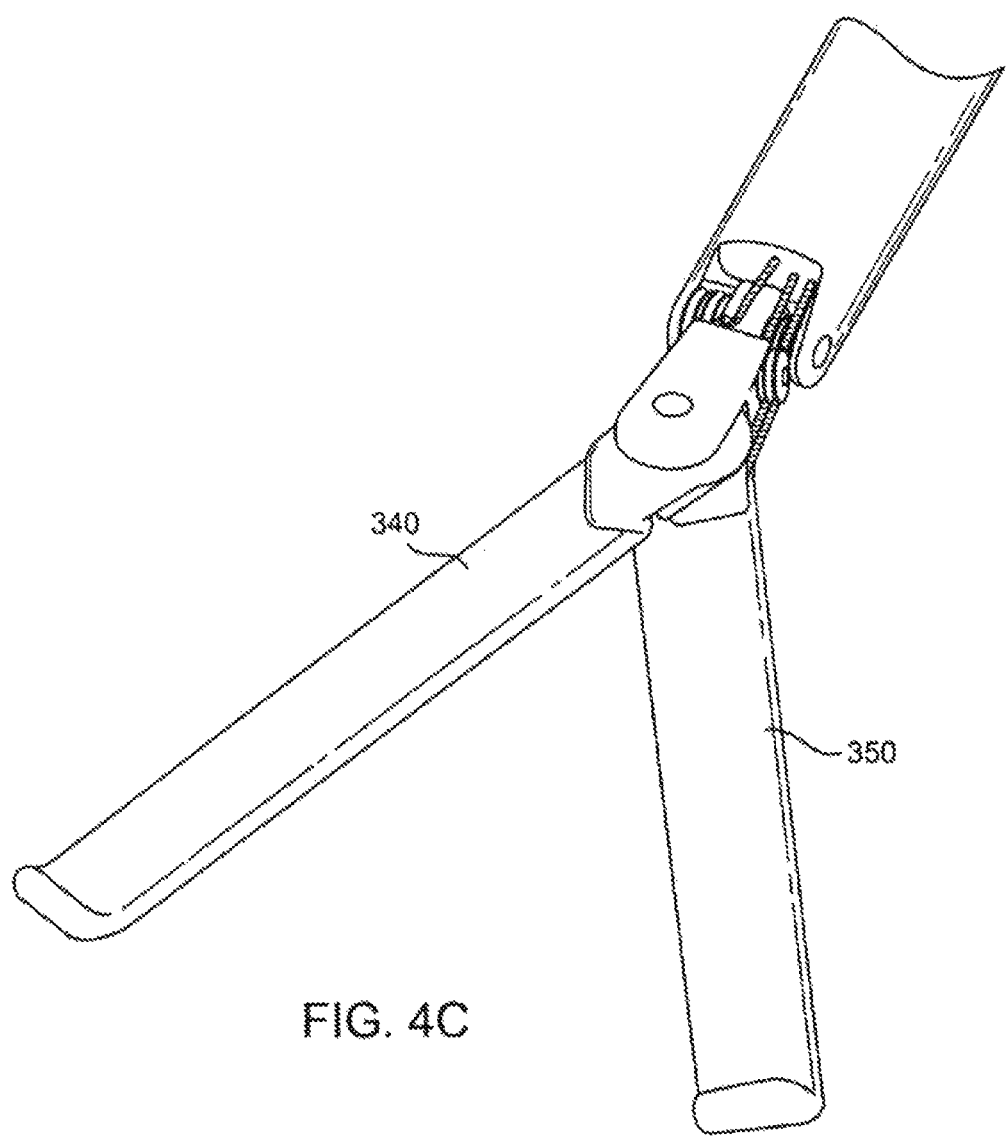
Figure 5B:
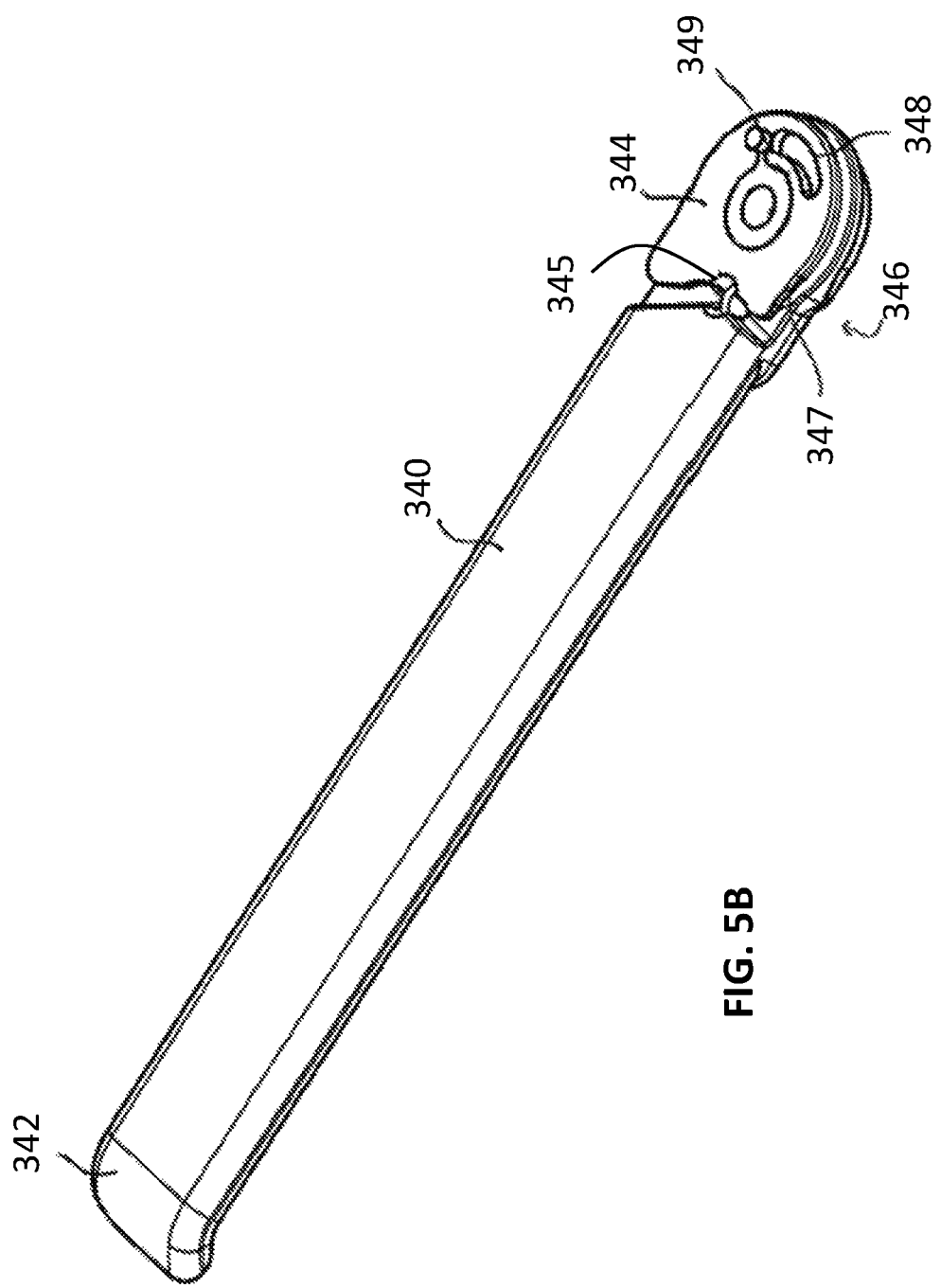
Figure 5C:
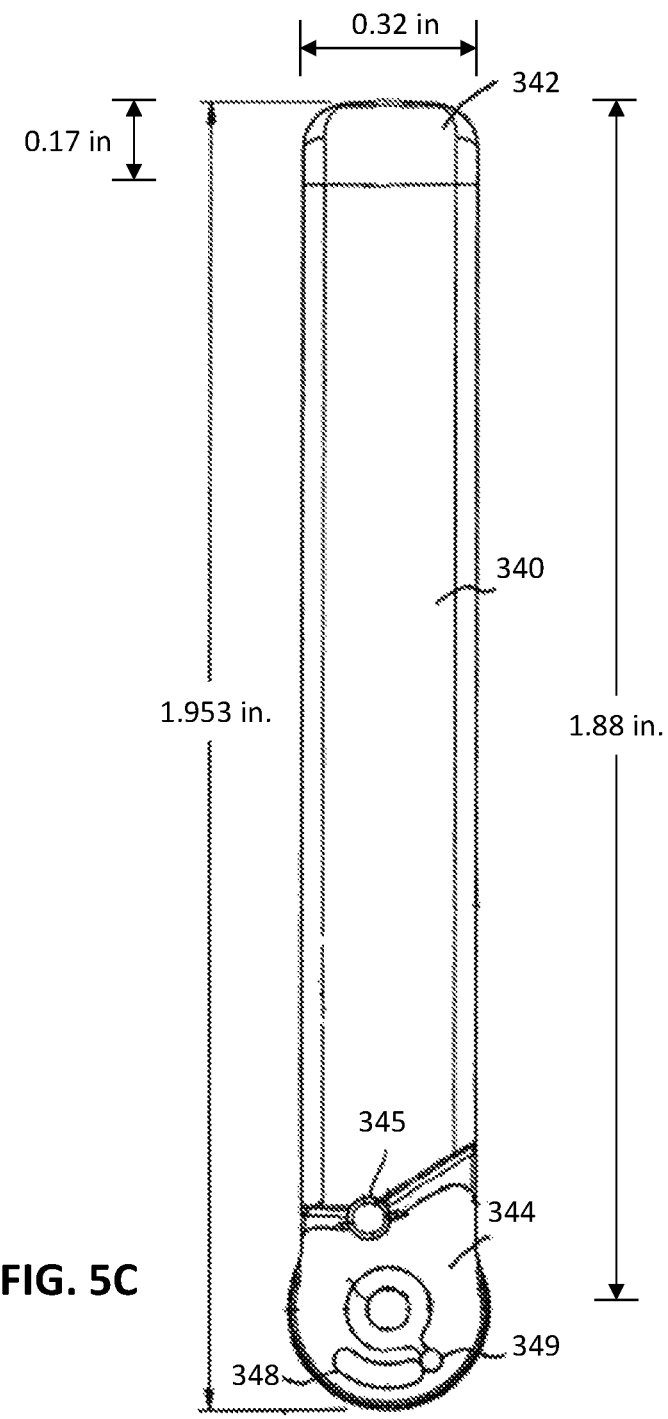
FIG. 5C is a rear plan view of the inner blade.
Figure 6A:
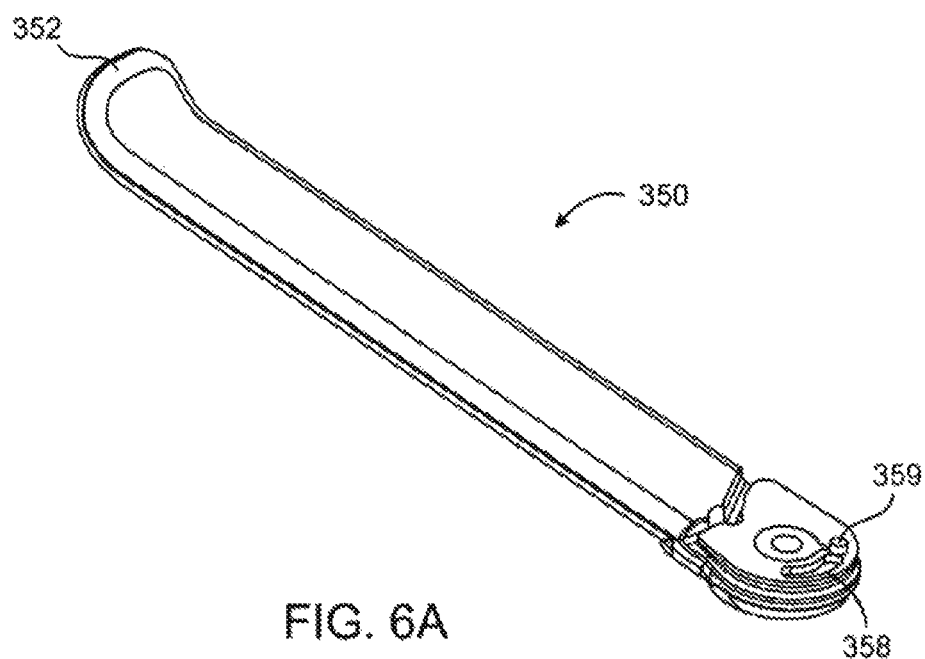
FIGS. 6A and 6B are front and rear perspective views of an outer blade of the retractor assembly.
Figure 6B:
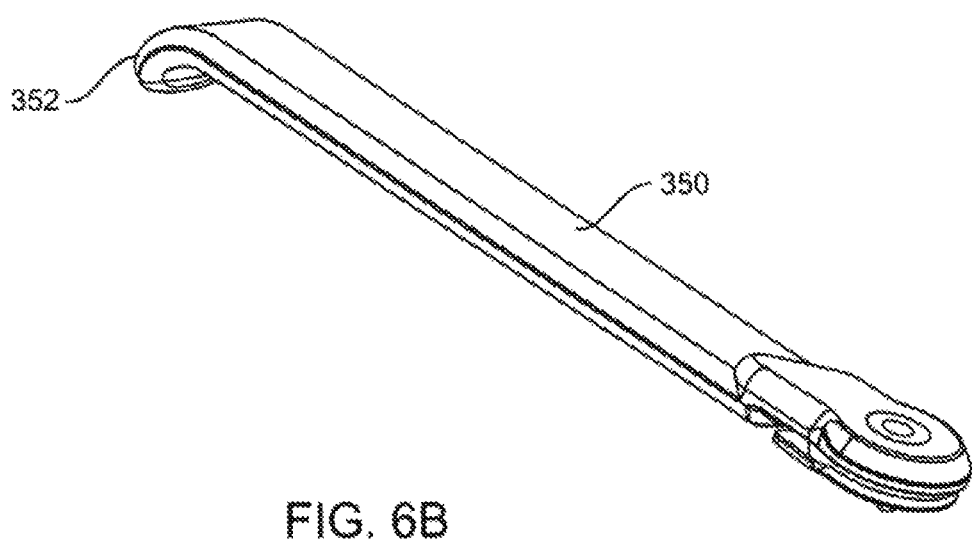
Figure 7A:
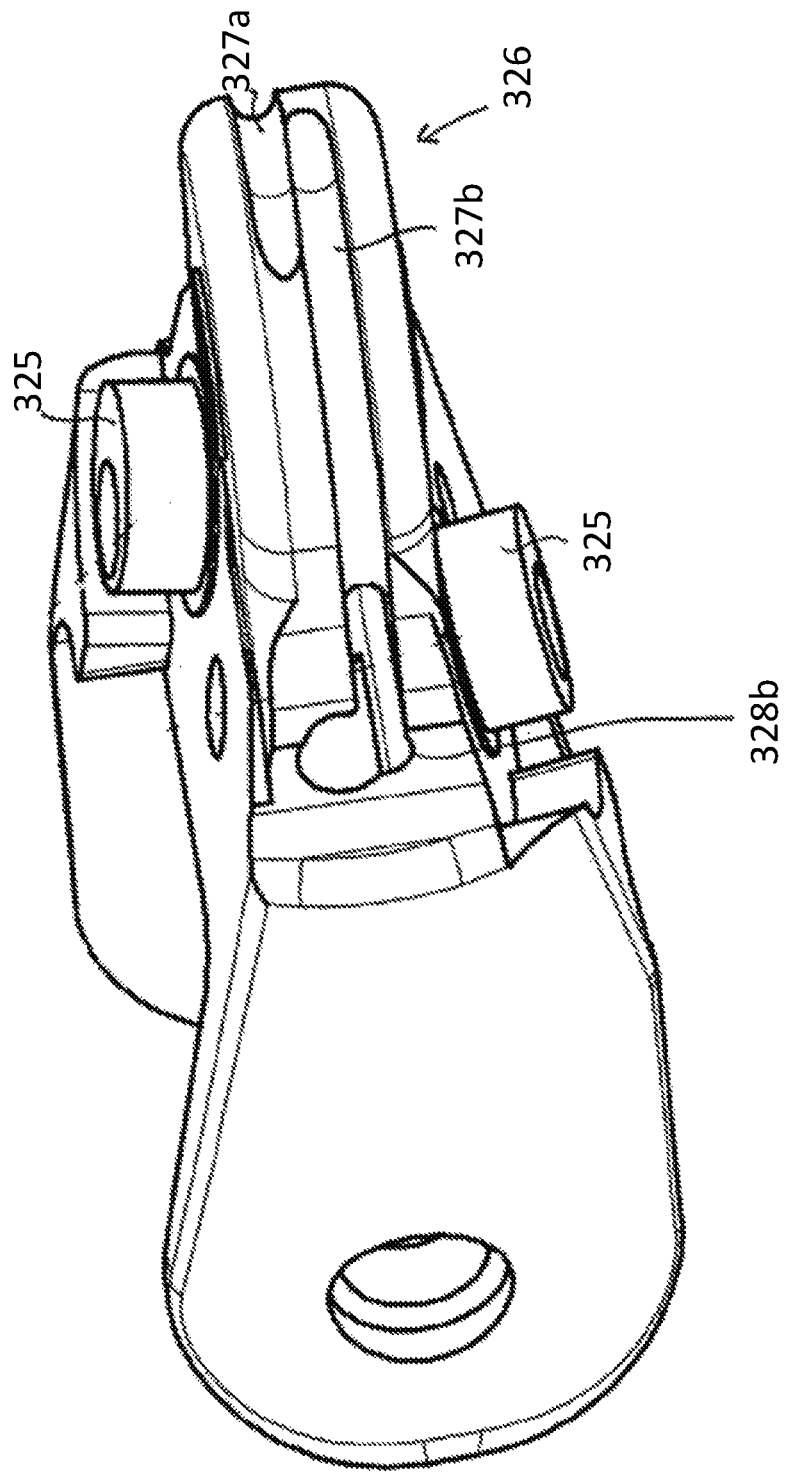
FIGS. 7A-7E are various views of a portion of the wrist assembly.
Figure 7B:
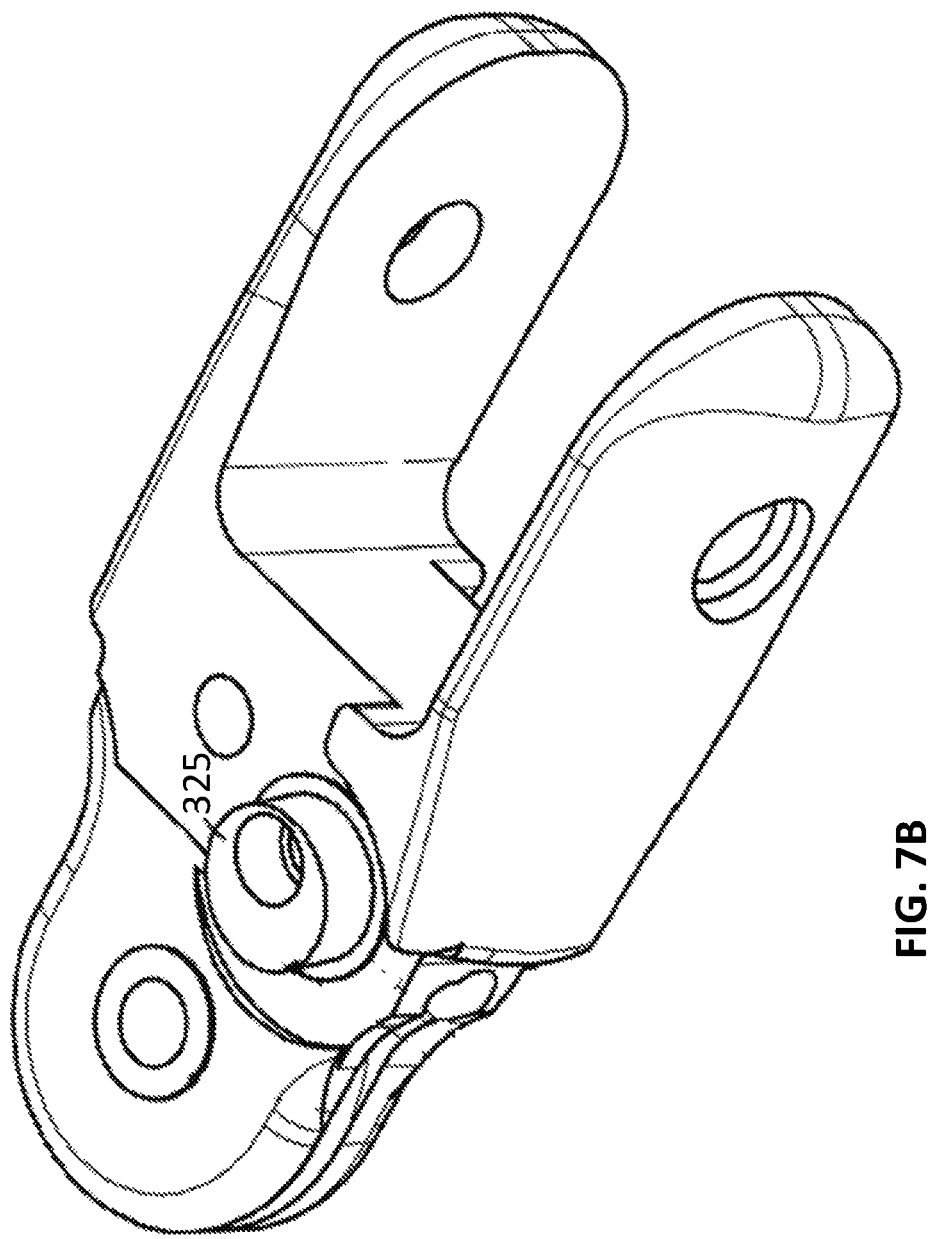
Figure 7C:
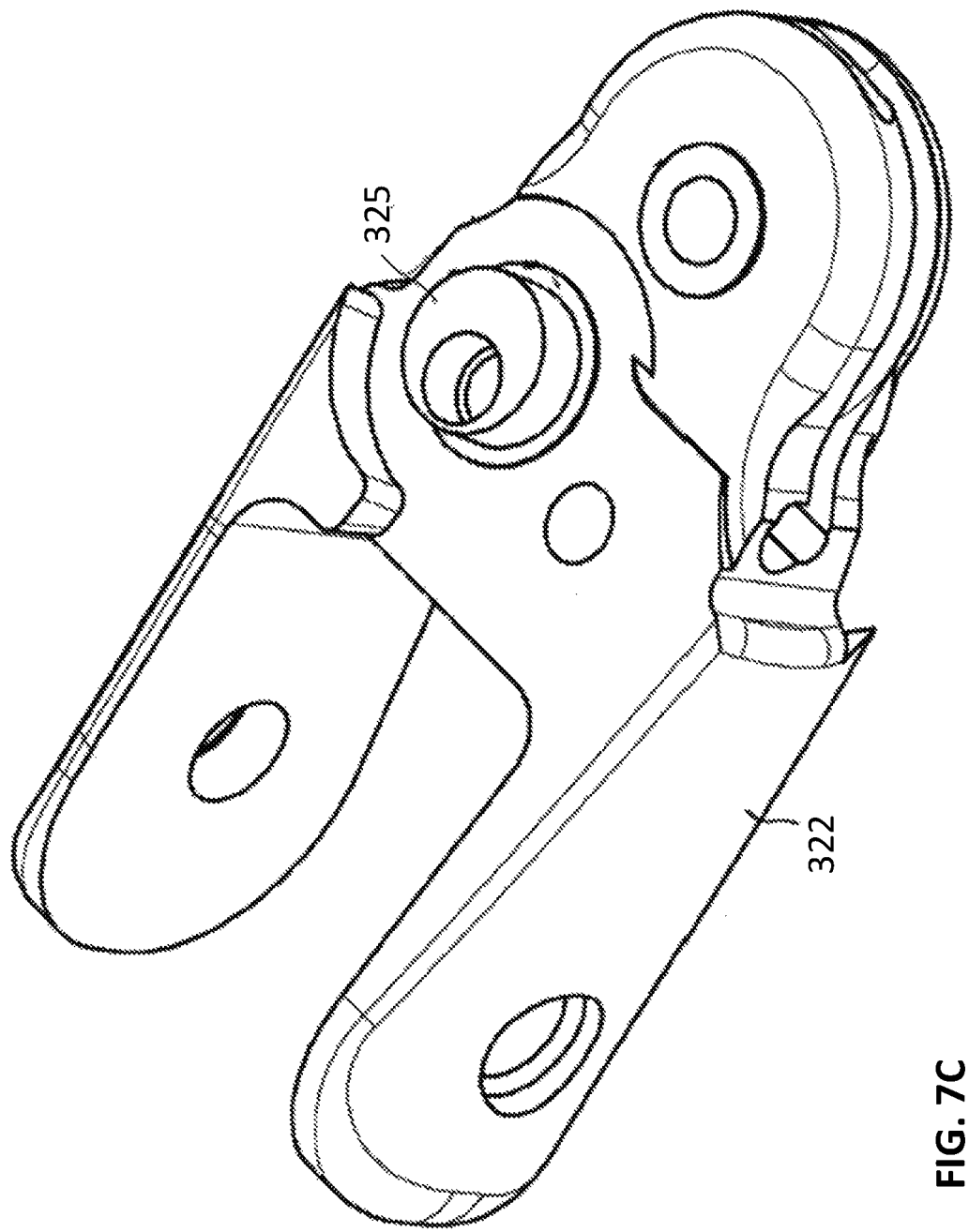
Figure 7D:
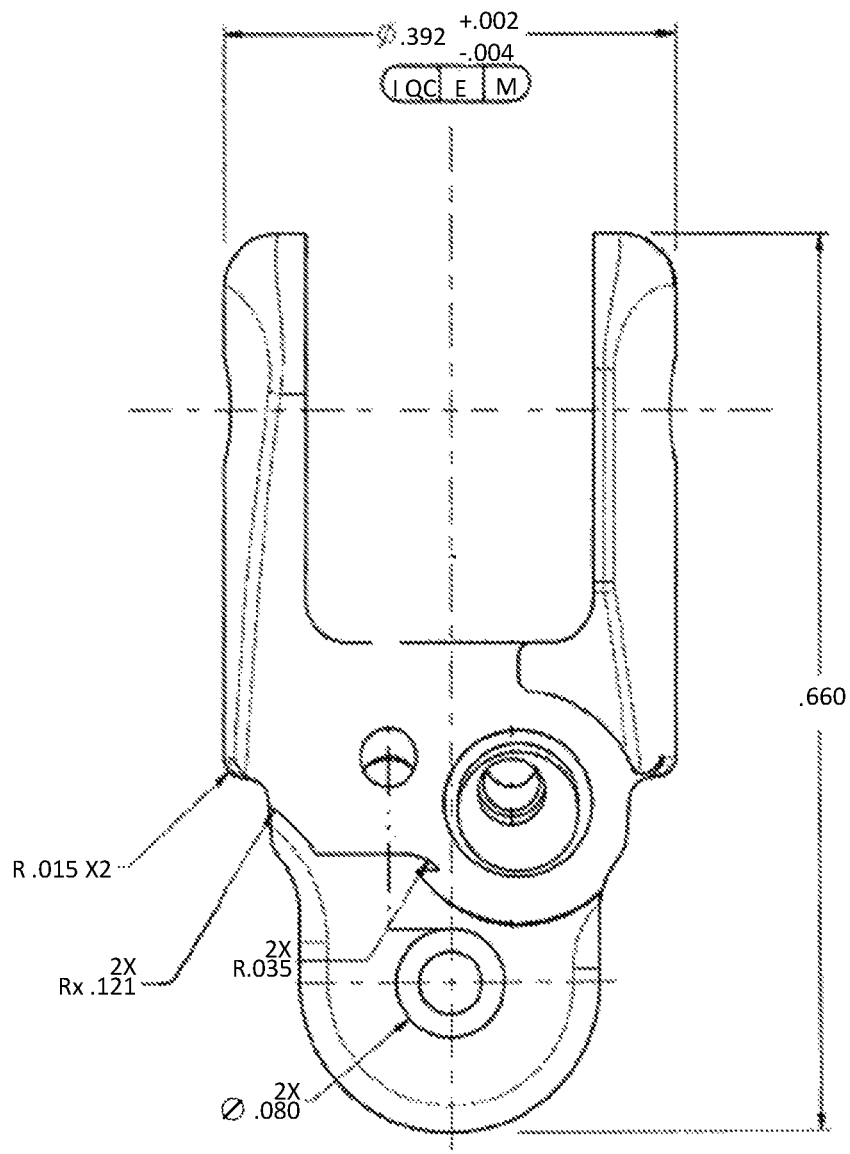
Figure 7E:
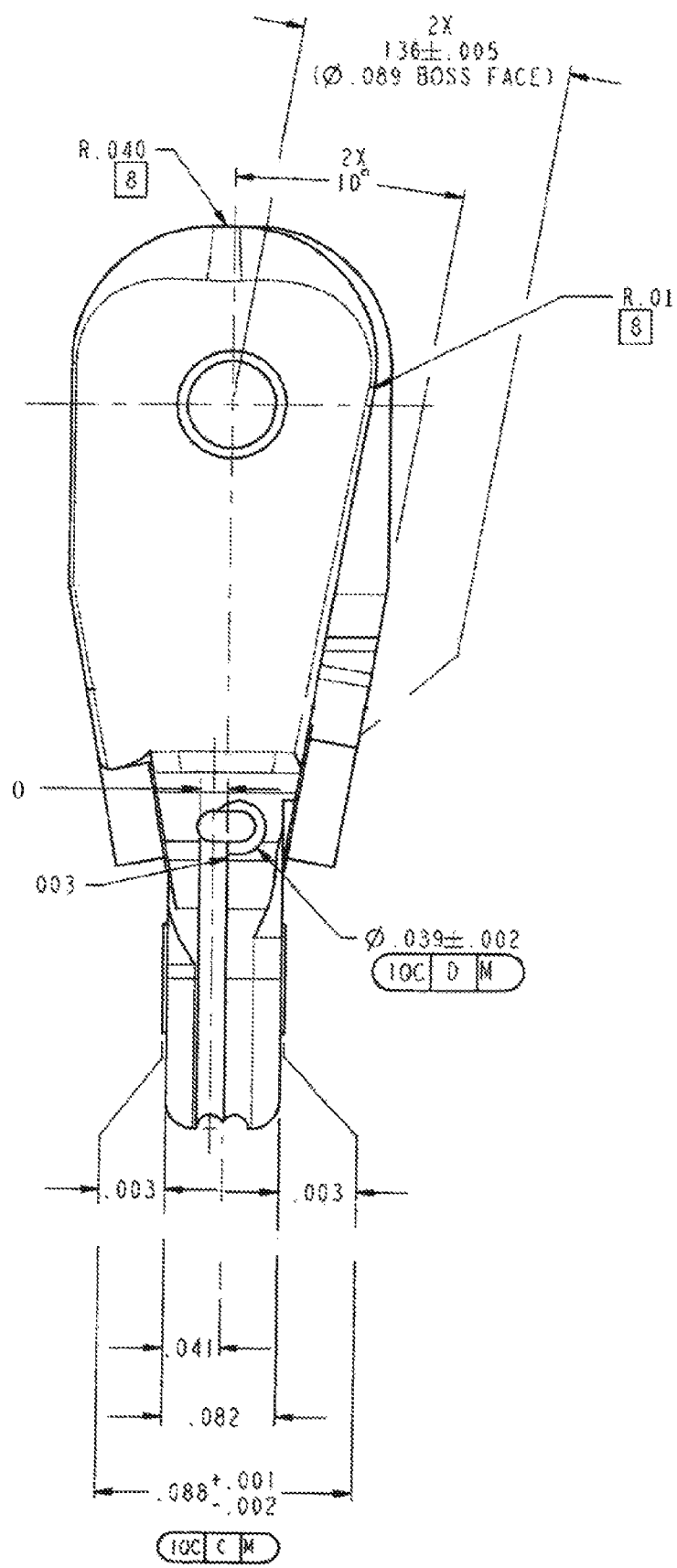
Figure 8A:
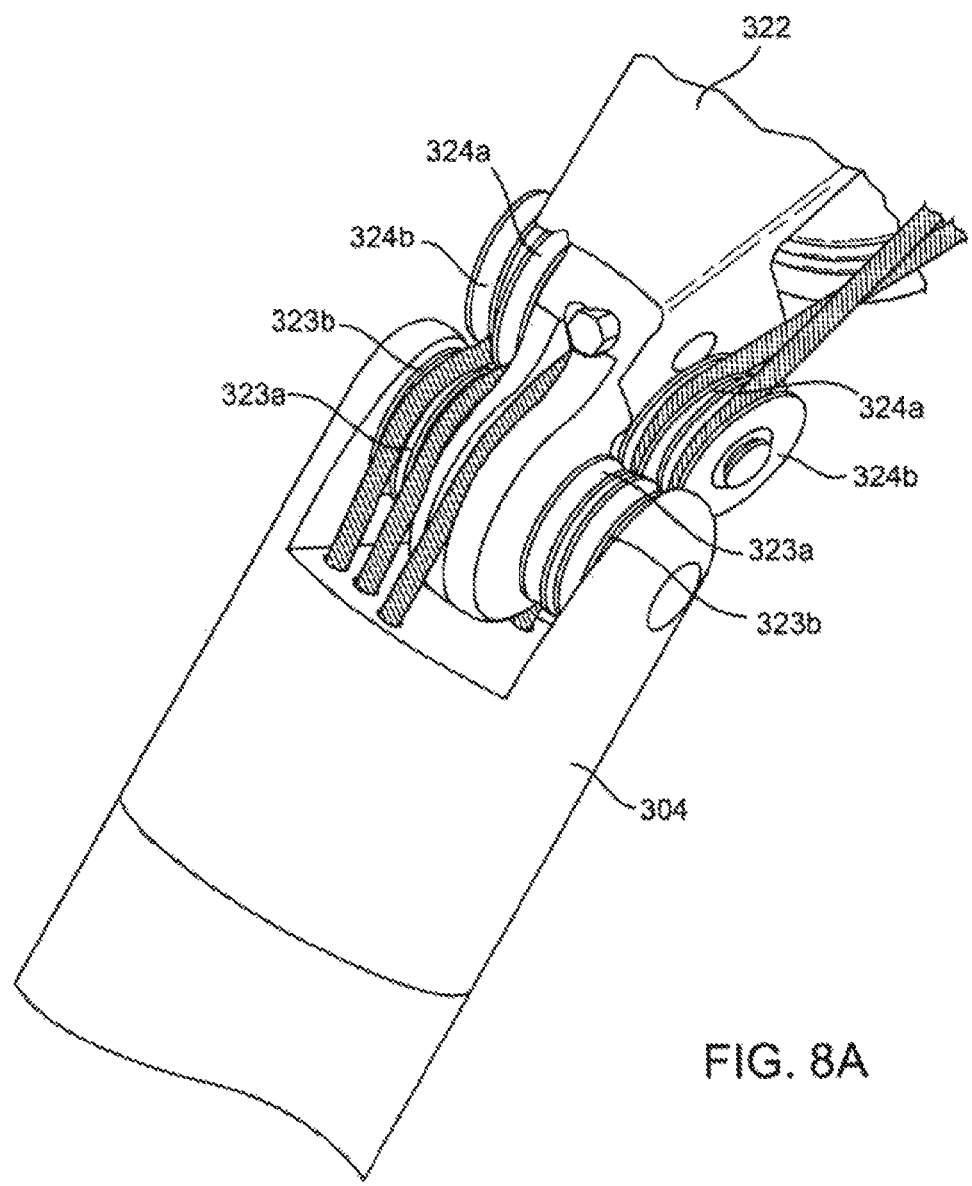
FIGS. 8A-8B are enlarged views of the wrist assembly.
Figure 8B:
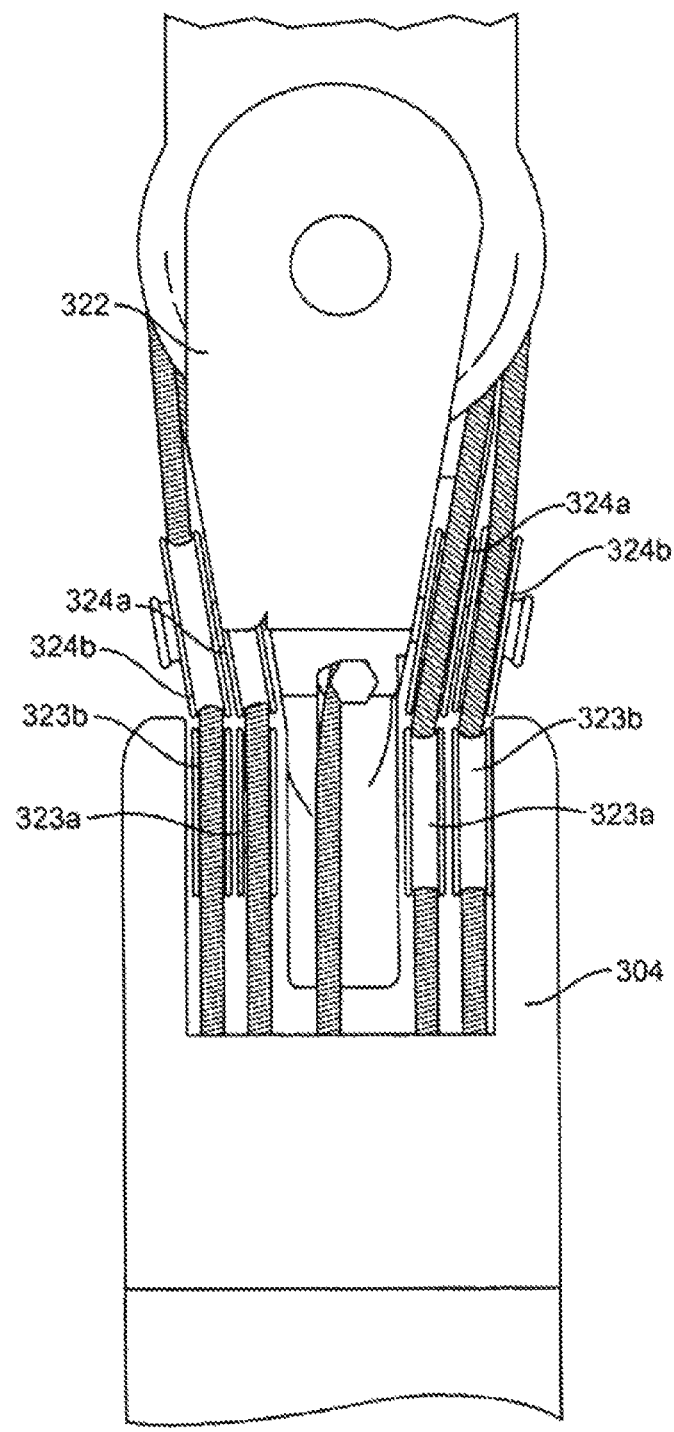
Figures 12A, 12B:
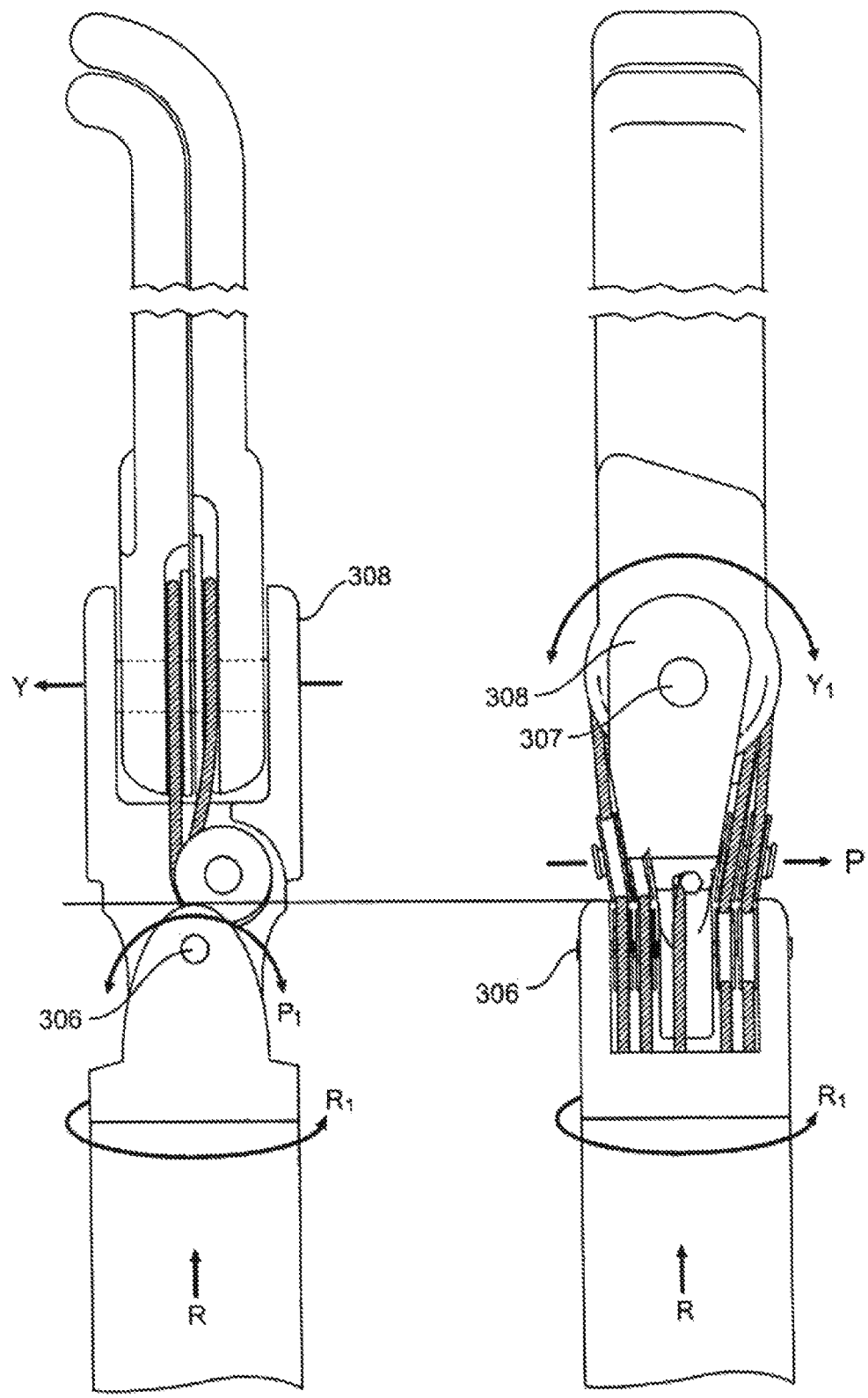
FIGS. 12A-12B are simplified views showing the possible articulation of the working end of the instrument.

FIGS. 4A-4C are enlarged perspective views of the working end 310 of the surgical instrument 300, including the wrist assembly 320 and retractor assembly 330. FIGS. 5A and 5B are front and rear perspective views of an inner blade 340 of the retractor assembly 330, and FIG. 5C is a rear plan view of the inner blade 340. FIGS. 6A and 6B are front and rear perspective views of an outer blade 350 of the retractor assembly 330. FIGS. 7A-7C are various perspective views and FIGS. 7D-7E are plan views of a portion of the wrist assembly 320. FIGS. 8A-8B are enlarged views of the wrist assembly 320. FIGS. 12A-12B are simplified views showing the possible articulation of the working end 310.

The proximal clevis assembly 304 is rotatably coupled to the end 305 of the shaft 302 such that the proximal clevis assembly 304 is rotatable about the axis of the shaft 302 (shown in FIGS. 12A-12B as axis R). This rotation of the proximal clevis assembly 304 about the shaft axis is referred to as the roll of the assembly 304 (shown in FIGS. 12A-12B as roll $R_1$). One end of the wrist assembly 320 is pivotally mounted in the proximal clevis assembly 304 by means of a pivotal connection 306. The wrist assembly 320 includes a rigid wrist member 322 which can rotate about the pivotal connection 306 (shown in FIGS. 12A-12B as axis P). This rotation about the pivotal connection 306 is referred to as the pivot or pitch of the wrist member 322 (shown in FIGS. 12A-12B as pitch $P_1$).

The retractor assembly 330 serves as the end effector of the surgical instrument 300 and is pivotally mounted on a second pivotal connection 307 provided in a distal clevis portion 308 of the wrist assembly 320. The retractor assembly 330 comprises an inner blade 340 and an outer blade 350, each including a mounting end 344, 354 pivotally mounted to the second pivotal connection 307. The blades 340, 350 also include free ends 342, 352, which are angularly displaceable about the second pivotal connection 307 toward and away from each other, and a body portion disposed between the mounting end 344, 354 and the free end 342, 352. In this embodiment, the free ends 342, 352 are provided with a slightly curved tip which extends at an angle relative to the plane defined by the body of the blades 340, 350. The curved tips enable the retractor blades 340, 350 to more securely grip the cardiac tissue, as will be described in greater detail below. In addition, the edges of the blades 340, 350 are blunt so as to avoid causing damage to the tissue being retracted.

FIGS. 4A and 4C show the blades 340, 350 of the retractor assembly 330 displaced away from each other in the open position, while FIG. 4B shows the blades 340, 350 of the retractor assembly 330 brought together in the closed position. In the embodiment shown in FIGS. 4A-4C, the outer blade 350 is slightly longer than the inner blade 340 so that the curved tip of the free end 342 of the inner blade 340 fits inside the curved tip of the free end 352 of the outer blade 350.

The retractor blade 340 includes a pulley portion 346 which defines a circumferentially extending channel 347 in which an elongate element in the form of, e.g., an activation cable, is carried. In this embodiment, a cylindrical crimp member is provided medially along the activation cable. This crimp member is received in the aperture 345 of the blade 340 to couple the cable and the blade 340 together. The ends of the activation cable are operatively coupled to a control interface provided on the control housing 303 such that linear movement of the activation cable actuates rotational movement of the blade 340. In other embodiments, two activation cables may be used to actuate rotation of the blade 340.

FIGS. 6A-6B illustrate the outer blade 350, which operates in substantially the same way as the inner blade 340. Each blade 340, 350 includes a slot 348, 358 and a protruding boss 349, 359. The boss 349 on the inner blade 340 is slidably received in the slot 359 of the outer blade 350, and the boss 359 on the outer blade 350 is slidably received in the slot 349 of the inner blade 340. The length of the slots 348, 358 and the relative positions of the slots 348, 358 and bosses 349, 359 limit the extent to which the blades 340, 350 can rotate relative to each other. One end of the slots 348, 358 correspond to the closed position of the blades 340, 350 and the other end of the slots 348, 358 correspond to the open position of the blades 340, 350. In this embodiment, the blades 340, 350 are configured to be angularly displaced from each other by a maximum of 60.degree. In other embodiments, the slots 348, 358 may be made shorter to decrease the maximum angular displacement, or made longer to increase the maximum angular displacement.

Each side of the wrist member 322 includes a pair of offset distal idler pulleys 324a-324b, which are mounted to pulley mounts 325, and a pair of pulleys 323a-323b, which are mounted at the pivotal connection 306 between the wrist assembly 320 and the proximal clevis assembly 304. The distal idler pulleys 324a-324b and pulleys 323a-323b function to route the activation cables through the wrist assembly 320 to the blades 340, 350. The idler pulleys 324a-324b are offset so that the fleet angles of the pulleys 324a-324b are optimized.

The wrist member 322 includes a pulley portion 326, which defines a pair of channels 327a-327b in which elongate elements (e.g., activation cables) are carried. These activation cables have a distal end received in the opening 328a-328b in the wrist member 322, and a proximal end operatively coupled to the controller interface of the controller housing 303. Alternatively, a single activation cable may be used, whereby a median portion of the cable is coupled to the wrist member 322 and the distal ends of the cable are operatively coupled to the controller interface.

A plurality of elongate elements, e.g., activation cables, are used to effect movement of the wrist assembly 320 and the retractor assembly 330. The activation cables pass from the wrist assembly 320 through appropriately positioned holes in the base region of the proximal clevis assembly 304, and internally along the shaft 302, toward the housing 303. The housing 303 includes a controller interface comprising driving members, e.g., in the form of spool assemblies for manipulating the activation cables. Additional details of a similar mechanisms for manipulating various surgical tools, including control housings and spool assemblies, can be found in U.S. Pat. No. 6,394,998, filed on Sep. 17, 1999, issued on May 28, 2002, and U.S. Pat. No. 6,902,560, filed on Jan. 6, 2004, issued on Jun. 7, 2005, the disclosures of which are incorporated by reference herein in their entireties.

The various components of the surgical instrument 300, and, in particular, the wrist assembly 320 and the retractor assembly 330, may be fabricated from surgical grade stainless steel. In the illustrated embodiment, each of the blades 340, 350 of the retractor assembly 330 have a width of approximately 6.6 mm and a thickness of approximately 1.77 mm. In addition, the edges along the length of the blades 340, 350 are curved at a radius of approximately 1.75 mm, the corners at the end portions are curved at a radius of approximately 2.5 mm, and the end portion 342 of the inner blade 340 is curved inward such that the inner surface has a radius of curvature of approximately 1.4 mm. In this embodiment, the outer blade 350 is slightly longer than the inner blade 340. Exemplary dimensions for the outer blade 350 are shown in FIG. 5C. The inner blade 340 is approximately 2 mm or 0.08 inches shorter in length. FIG. 7D shows exemplary dimensions in inches for the wrist member 322. In other embodiments, the blades 340, 350, wrist member 322, and other components of the instrument 300 may be provided in different sizes and all of the dimensions may vary. In particular, it may be desirable for a manufacturer to provide retractor instruments in a variety of effective lengths, such as 35 mm, 40 mm, or 50 mm, so as to accommodate a variety of patient anatomies. The effective length of the blades 340, 350 is measured from the end of the wrist member 322 to the tip of the distal ends 342, 352.

When the blades 340, 350 are in the closed position, the blades 340, 350 are substantially overlapped so that the entire retractor assembly 330 has a closed width approximately equal to the diameter of the shaft 302, which can be, e.g., 8 mm. This enables the retractor assembly 330 to be inserted through small-diameter cannula sleeves (e.g., 8.5 mm inner diameter cannula sleeves) to the internal surgical site. In the illustrated embodiment, the blades 340, 350 have substantially identical widths which are substantially constant along the length of the blades. This differs with scissor tools, which typically have blades that narrow towards the tips so as to minimize the surface area to improve the ease with which the scissors may be operated to cut through tissue and other materials. In contrast, the constant width of the blades 340, 350 maximizes the size of the blade surface for use in retracting tissue when opened, while still enabling the insertion of the closed blades 340, 350 through the cannula. In this embodiment, the blades 340, 350, have a substantially rectangular profile, with curved end portions 342, 352, which reduce the risk of tissue damage that may be caused by sharp corners. In addition, the low profile and thinness of the retractor blades 340, 350 conceal only a small portion of atrial tissue when deployed. This may result in greater exposure along with less absorption of light.

An application of the retractor instrument 300 will be described below. In this embodiment, the robotic surgical system 200 comprises the da Vinci S Surgical System. Two articulated instrument arms and a three-dimensional high-magnification 30.degree. camera were port-introduced into the right thorax of the patient. A fourth instrument arm is provided with the retractor instrument 300, described above. This fourth instrument arm allows for six degrees of freedom of movement, in addition to adjustable separation of the end portions 342, 352 of the retractor blades 340, 350. The retractor instrument 300 is introduced into the chest via a 10-mm trocar.

Figure 10:
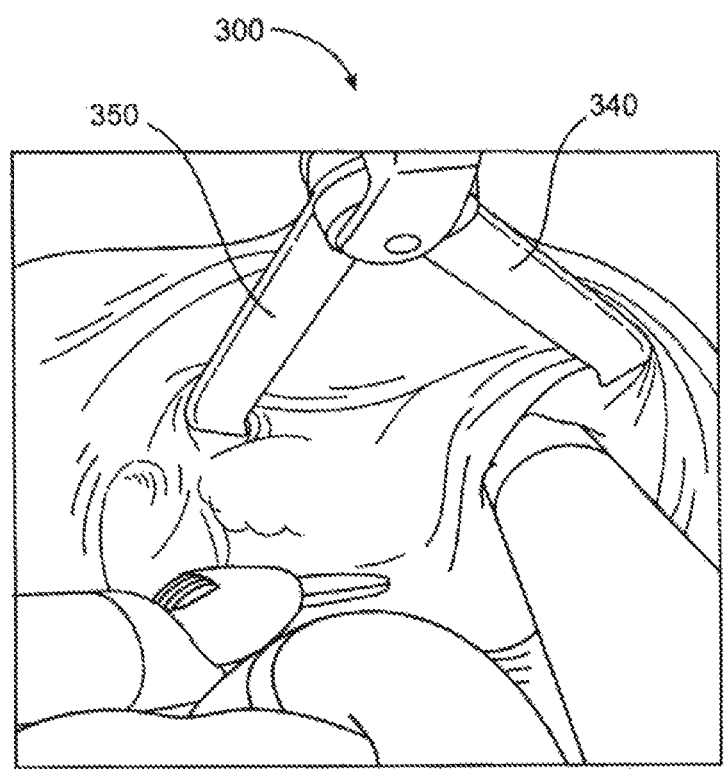
FIG. 10 is a view of the retractor instrument deployed inside the left atrium.

FIG. 10 is a view of the retractor instrument 300 deployed inside the left atrium. After the retractor wrist assembly 320 is visible within the thorax by the console surgeon, the console surgeon positions and spreads the blades 340, 350 inside the left atrium. To reposition the blades 340, 350, the surgeon may toggle control back and forth between the instrument arm and retractor arm using the foot pedal clutch of the da Vinci system. The retractor blades 340, 350 are then separated gently and the tips positioned near each fibrous trigone. By reactivating the instrument arm with the clutch, the atrial retractor 300 remains in position and leaflet repairs may be performed using the two instrument arms.

Upon completion of leaflet repairs and subvalvular work, the blades 340, 350 may be repositioned to optimize exposure of the right fibrous trigone and posterior commissure for annuloplasty band insertion using either sutures or nitinol clips. Generally, a third maneuver is utilized for optimal access of the left fibrous trigone and anterior commissure. Before removing the device and closing the atrium, the retractor blades 340, 350 may be lowered to establish normal atrial geometry for saline testing in order to assess valve competency.

In accordance with aspects of the present invention, dynamic atrial retraction may be provided in order to provide different exposure views based on surgical needs. FIG. 9 is a simplified view of a mitral valve 900 with an annuloplasty ring 930 attached thereto. In order to attach the ring 930 to the annulus 912 of the valve 900, the surgeon must have exposure to the trigones to which the ring 930 is attached. Due to the limited viewing angle of the imaging system, only a portion of the annulus 912 may be visible at any point during the procedure. For example, in order to attach the ring 930 to the left trigone, it may be desirable to provide a first view 902. After the attachment is complete, it would be desirable to reposition the imaging system to provide a second view 904 of the right trigone. Conventional retractors may not be able to provide optimal views of both the left and right trigones. In contrast, the retractor instrument 300 may be repositioned during the procedure so as to provide optimal exposure of the region currently being imaged by the surgeon.

Figure 11:
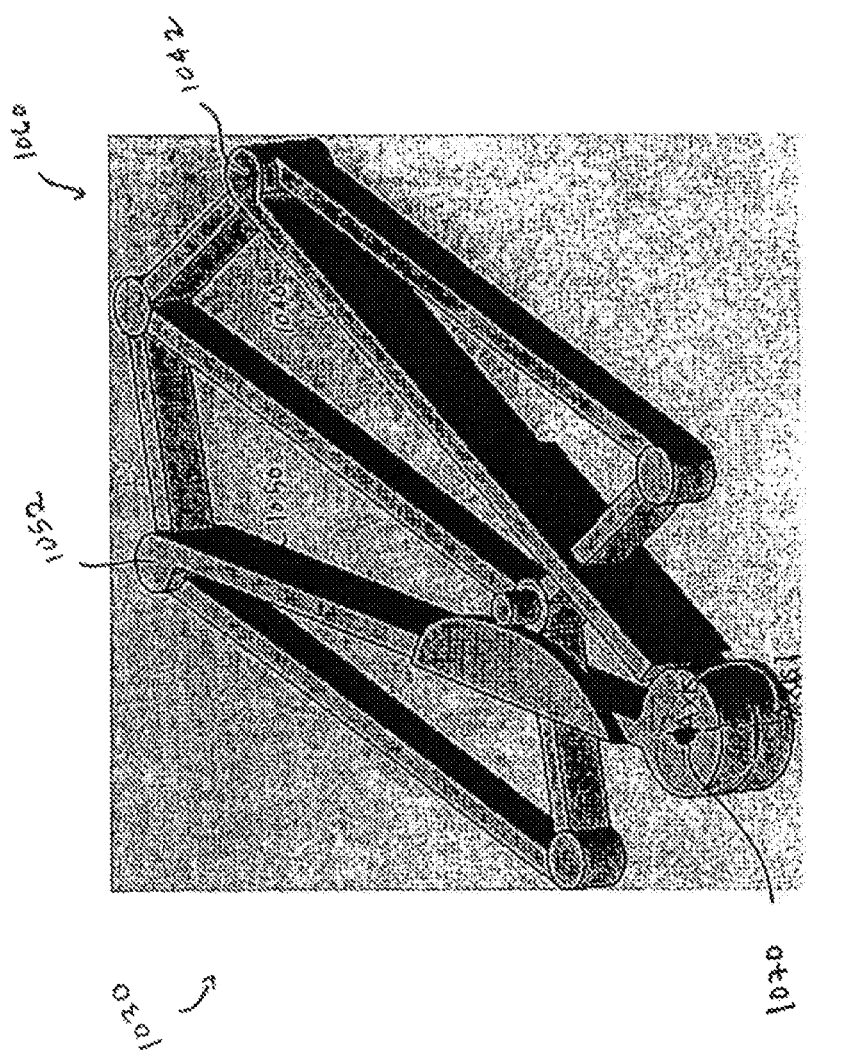
FIG. 11 illustrates a retractor assembly, in accordance with another embodiment of the present invention.

In accordance with other embodiments of the present invention, different retractor blade geometries and configurations may be used. For example, FIG. 10 illustrates a retractor assembly 1030, in accordance with another embodiment of the present invention. The retractor assembly 1030 includes two rotatable blades 1040, 1050 supporting an expansion structure 1060. The blades 1040, 1050 have a proximal end rotatably coupled to a pivotal connection 1070 and distal ends 1042, 1052 which are angularly displaceable about the pivotal connection 1070. As the distal ends 1042, 1052 are angularly displaced, the expansion structure expands to the open configuration shown in FIG. 11. This configuration serves to provide a large surface region for retracting tissue.

In accordance with other embodiments of the present invention, a non-rigid webbing may be provided between the retractor blades so as to enable the capture of a greater amount of tissue and prevent tissue from protruding between the blades. This webbing may comprise a net or mesh which is coupled to the blades such that when the blades are in the closed position, the webbing is collapsed and may pass through the cannula. When the blades are in the open position, the webbing is expanded to provide a large surface area.

Embodiments of the present invention may provide various advantages not provided by prior art systems. The overall size of the retractor assembly 330 may be substantially equal to existing instruments for minimally invasive surgery, such as the EndoWrist instruments by Intuitive Surgical, Inc. This can enable the instrument to be used with existing equipment.

In addition, the retractor assembly 330 may be deployed within the thoracic cavity through a sealed cannula (e.g., through an 8-mm to 12-mm port). As a result, $CO_2$ insufflation is maintainable, thereby allowing an endoscopic procedure.

Due to the curved end portions of the retractor blades, the septum and left atrium may be maintained in a stable position without slipping during the duration of the mitral valve procedure. In other embodiments, the curved end portions of the retractor blades may be longer or shorter than the end portions shown and described herein. For example, longer curved end portions may enable the surgeon to achieve a more secure grasp of the atrial tissue. If longer curved end portions are used, the angle of curvature may be decreased so as to permit the retractor assembly to pass through the same size cannula.

Furthermore, the retractor assembly 330 allows safe and stable exposure of the mitral valve when introduced through a port in a 5 cm.times.10 cm surface area lateral to the sternum, thereby making the quality of the mitral valve exposure less dependent on port location.

The retractor assembly 330 may enable dynamic atrial retraction for exposure during complex procedure steps of the valve reconstruction procedure (e.g., annuloplasty ring placement) in an endoscopic environment. The retractor instrument 300 may be fully articulating for flexibility in exposing the mitral valve in multiple planes.

Finally, the retractor instrument 300 may be provided as a single preassembled device, eliminating the need to assemble the retractor within the patient after insertion.

The above-described arrangements of apparatus and methods are merely illustrative of applications of the principles of this invention and many other embodiments and modifications may be made without departing from the spirit and scope of the invention as defined in the claims. For instance, the robotic arms may have other configurations. Different actuation mechanisms other than activating cables may be used to manipulate the wrist member and end effector. The scope of the invention should, therefore, be determined not with reference to the above description, but instead should be determined with reference to the appended claims along with their full scope of equivalents.

In addition, in the illustrated embodiment, the blades 340, 350 open or close in unison. However, in other embodiments, each of the blades 340, 350 may be configured to be angularly displaced independently of the other blade 340, 350, thereby enabling a wider variety of deployment configurations. In addition, in some embodiments, the wrist assembly 320 is configured for pitch and roll movement only, while the retractor assembly 330 is configured for opening and closing movement only. In other embodiments, the surgical instrument 300 may have greater or fewer degrees of movement. In particular, in some embodiments, the retractor assembly 330 may be further configured for yaw and/or roll movement. For example, in the illustrated embodiment, the blades 340, 350 can rotate together about the pivotal connection 307 (shown in FIG. 12A as axis Y). This joint rotation of the blades 340, 350 about the axis Y is referred to as the yaw of the blades 340, 350.

Therefore, it should be understood that the invention can be practiced with modification and alteration within the spirit and scope of the appended claims. The description is not intended to be exhaustive or to limit the invention to the precise form disclosed. It should be understood that the invention can be practiced with modification and alteration and that the invention be limited only by the claims and the equivalents thereof.

The invention claimed is:

1. A method of retracting tissue, the method performed by a processing system, the method comprising
receiving instructions for operating a minimally invasive surgical instrument that includes an elongate shaft coupled at a distal end to a retractor assembly, the instructions including
moving the retractor assembly to a closed configuration in which first and second blades of the retractor assembly have a first angular displacement about is pivot assembly and in which an expansion structure supported by the first and second blades is collapsed and
moving the retractor assembly to an open configuration in which first and second blades have a second angular displacement about the pivot assembly, wherein the second angular displacement is greater than the first angular displacement and in which the expansion structure is expanded to bound an expansion region, wherein the expansion region bounded by the expanded expansion structure is greater than the angular displacement region bounded by the blades.

2. The method of claim 1 wherein the expansion structure includes a plurality of linkages pivotally coupled to the first and second blades.

3. The method of claim 1 wherein the first blade has a distal end coupled to a first linkage and to a second linkage.

4. The method of claim 3 wherein the second blade has a distal end coupled to a third linkage, wherein the third linkage is pivotally coupled to the first linkage.

5. The method of claim 4 wherein the second linkage is pivotally coupled to a fourth linkage, wherein the fourth linkage extends through the first blade.

6. The method of claim 5 wherein a fifth linkage extends between the first and second blades such that the fifth linkage moves proximally toward the pivot assembly as the retractor assembly moves to the open configuration.

7. The method of claim 6 wherein the fifth linkage is coupled between the first and fourth linkages.

8. The method of claim 1 wherein the retractor assembly includes webbing extending between the first and second blades.

9. The method of claim 8 wherein the webbing includes a non-rigid mesh.

* * * * *